United States Patent
Pagano et al.

(10) Patent No.: US 6,310,033 B1
(45) Date of Patent: Oct. 30, 2001

(54) FRAGRANCE MATERIALS

(75) Inventors: Alex R. Pagano, Morris Township, NJ (US); Walter C. Frank, Holland, PA (US); Vrej Jubian, Plainsboro, NJ (US)

(73) Assignee: Bush Boake Allen Inc., Montvale, NJ (US)

( * ) Notice: Subject to any disclaimer, the term of this patent is extended or adjusted under 35 U.S.C. 154(b) by 0 days.

(21) Appl. No.: 09/473,503

(22) Filed: Dec. 28, 1999

(51) Int. Cl.$^7$ ........................................................ A61K 7/46
(52) U.S. Cl. ................... 512/27; 512/8; 512/11; 512/20; 512/25; 512/6; 510/101
(58) Field of Search .................. 512/8, 11, 20, 512/25, 6, 27; 510/101

(56) References Cited

U.S. PATENT DOCUMENTS

| | | | |
|---|---|---|---|
| 4,193,934 | * | 3/1980 | Bauer et al. ............................ 512/6 |
| 5,888,962 | * | 3/1999 | Frank et al. ........................... 512/22 |
| 5,919,752 | * | 7/1999 | Morelli et al. ......................... 512/1 |
| 5,958,870 | | 9/1999 | Declerq et al. . |

FOREIGN PATENT DOCUMENTS

| | | | |
|---|---|---|---|
| 2051319 | * | 4/1972 | (DE) . |
| 405427 | * | 1/1991 | (EP) . |
| 0908439 | | 4/1999 | (EP) . |

OTHER PUBLICATIONS

"Systematic Synthesis of Odoriferous Substances. Odor Relations of the Isobutenyl & Phenyl Groups.", Sturm, Wolfgang; Parfuem. Kosmet. (1974), 55(12), 351–5. (Abstract).*

* cited by examiner

Primary Examiner—Jill Warden
Assistant Examiner—Monique T. Cole
(74) Attorney, Agent, or Firm—Gibbons, Del Deo, Dolan, Griffinger & Vecchione

(57) ABSTRACT

The use of substituted 5-phenylpentan-1-ols, 5-phenylpentanals, 5-phenylpentanitriles, 5-phenylpentanoic acid and lower alkyl esters thereof and 5-phenylpentanyl esters of $C_1$–$C_6$ aliphatic acids as fragrance materials is disclosed. The subject fragrance materials are, in large measure, novel compounds. The subject materials possess unique fragrance notes and are cost-effective materials.

3 Claims, No Drawings

FRAGRANCE MATERIALS

This invention relates to the use of substituted phenylpentane derivatives as perfumery materials, and includes novel perfumery compounds.

BACKGROUND OF THE INVENTION

Many compounds have been described in the literature as-fragrance materials. As is the case with many classes of compounds having varied utilities, of the many compounds that are known to possess pleasing fragrance notes, only a very small portion are utilized commercially. There are several reasons for this, notably toxicological constraints, environmental considerations, biodegradability, performance, and cost effectiveness. While all of these factors must be carefully weighed in consideration of whether to introduce a new fragrance material, perhaps the most important factors are performance and cost. Performance properties include odor activity, notes, and aesthetics; substantivity; and solubility. The cost effectiveness involves manufacture costs and the amount of the compound required to impart fragrance to a consumable product. Of course, the lower the amount of fragrance material required, the higher its cost effectiveness. Many materials have met some of the above-mentioned criteria, yet have not been successful because of disappointing ratios of cost versus performance.

It must further be borne in mind that, because fragrance materials are by nature utilized in comparatively small quantities, only a very few benefit from the cost efficiency of large-scale production. All of these factors, combined with the tendency in many countries to take a more rigid regulatory position concerning ingredients in consumable products, have acted to hamper the introduction of new fragrance materials in recent years.

There is an on-going need for new fragrance materials that can be readily synthesized from relatively inexpensive raw materials, meet the criteria set forth above, possess unique fragrance notes and, perhaps most importantly, are cost-effective in use. Such materials are provided in accordance with the present invention.

SUMMARY OF THE INVENTION

The invention relates to the use of substituted 5-phenylpentan-1-ols, 5-phenylpentanals, 5-phenylpentanitriles, 5-phenylpentanoic acid and lower alkyl esters thereof and 5-phenylpentan-1-yl esters of $C_{1-C6}$ aliphatic acids as fragrance materials. The disclosed fragrance materials are, in large measure, novel compounds.

DETAILED DESCRIPTION OF THE INVENTION

The compounds found to possess attractive fragrance properties in accordance with the present invention are represented by the formula

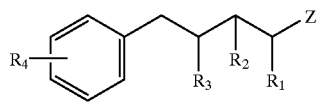

wherein each of $R_1$, $R_2$ and $R_3$ is independently selected from the group consisting of hydrogen, methyl and ethyl; $R_4$ is selected from the group consisting of hydrogen, $C_{1-4}$ lower alkyl and $C_{1-4}$ lower alkoxy; and Z is selected from the group consisting of —CHO, —CN, —CH$_2$OH, —COOH, —COOR, and —CH$_2$OC(O)R wherein R is lower alkyl, with the proviso that, when Z is—CHO, at least $R_3$ is other than hydrogen.

Certain compounds within the scope of the present invention are novel, i.e. those represented by the above formula wherein each of $R_1$, $R_2$ and $R_3$ is independently selected from the group consisting of hydrogen, methyl and ethyl; $R_4$ is selected from the group consisting of hydrogen, $C_{1-4}$ lower alkyl and $C_{1-4}$ lower alkoxy; and Z is selected from the group consisting of —CHO, —CH$_2$OH, —COOH, —COOR, and —CH$_2$OC(O)R wherein R is lower alkyl with the proviso that, when Z is —CHO, at least $R_1$ and $R_3$ are other then hydrogen, when Z is —CH$_2$OH, $R_1$ is hydrogen and at least one of $R_2$, $R_3$ and $R_4$ is other than hydrogen, and when Z is —COOCH$_3$, at least $R_1$ is other than hydrogen.

Preferred fragrance materials in accordance with the present invention are compounds represented by the above formula wherein Z is selected from —CHO, —CN, —CH$_2$OH, —COOH and —COOR wherein R is lower alkyl. Preferably, at least one of $R_1$, $R_2$ and $R_3$ is methyl or ethyl, in the order $R_3$, $R_1$ and $R_2$. The $R_4$ substituent on the phenyl ring can be ortho, meta or para to the bond to the pentane chain, preferably para.

The term "lower alkyl" as utilized herein shall mean both straight- or branched- chain alkyl radicals having from one to six carbon atoms, unless designated otherwise. This definition applies as well to the alkyl portion of lower alkoxy radicals as a meaning for $R_4$.

Preferred fragrance materials in accordance with the present invention include the following:

2-Methyl-5-phenylpentanenitrile
2-Methyl-5-phenylpentyl acetate
4-Methyl-5-phenylpentanenitrile
4-Methyl-5-phenylpentan-1-ol
4-Methyl-5-phenylpentanal
2,4-Dimethyl-5-phenylpentanitrile
2,4-Dimethyl-5-phenylpentan-1-ol
2,4-Dimethyl-5-phenylpentanal
Methyl 4-methyl-5-phenylpentanate
3-Ethyl-5-phenylpentanenitrile.

Compounds of the above formula wherein Z is —CN can be prepared from the corresponding substituted 3-phenylpropanal, known compounds, by reaction with cyanoacetic acid under alkaline conditions in the presence of an organic solvent. For example, 4-methyl-5-phenylpentanitrile can be prepared by the reaction of 2-methyl-3phenylpropanal. The substituted 5-phenylpentanitriles can conveniently be converted to the corresponding 5-phenylpentanals by known techniques, for example, by reaction with diisobutylaluminum hydride in a suitable organic solvent such as, for example, toluene. The substituted 5-phenylpentanals may then be converted to the corresponding substituted 5-phenyl-pentan-1-ols by reduction with hydrogen over a suitable catalyst, such as nickel on silica or palladium on carbon. The subject substituted 5phenylpentanals are also readily converted to the corresponding substituted 5-phenylpentanoic acids by oxidation with oxygen over a suitable catalyst.

The 2-methyl-5-phenyl aldehyde derivatives are conveniently prepared by a number of methods known in the art. For example, by an Aldol condensation between 3-phenylpropanal and proprionaldehyde, followed by hydrogenation of the resulting α,β-unsaturated aldehyde to form the saturated aldehyde, 2-methyl-5-phenylpentanal. This aldehyde is the direct precursor for the alcohol, 2-methyl-5-phenylpentan-1-ol via reduction with, e.g. sodium borohydride, as well as the nitrile, 2,4-dimethyl-5-phenyl-pentanitrile via oxidation dehydration chemistry by reaction of hydroxylamine/formic acid as described above. Alternatively, aldehyde derivatives may be prepared by oxidation of the corresponding primary alcohol, i.e. 2-methyl-5-phenylpentan-1-ol, a known compound. The corresponding nitrile, 2-methyl-5-phenylpentanenitrile, is prepared by converting the aldehyde via reaction with hydroxylamine to form the aldoxime intermediate and subsequent formic acid catalyzed dehydration. The primary alcohol may also be converted to the corresponding acid as described above.

The 2,4-dimethyl-5-phenylpentan-1-yl derivatives in accordance with the present invention can be prepared by a variety of ways. For example, by an Aldol condensation between 2-methyl-3-phenylpropanal and proprionaldehyde, followed by hydrogenation of the resulting $\alpha,\beta$-unsaturated aldehyde to form the saturated aldehyde, 2,4-dimethyl-5-phenylpentanal as described above. This aldehyde is the direct precursor for the alcohol, 2,4-dimethyl-5-phenylpentan-1-ol via reduction with, e.g. sodium borohydride, as well as the nitrile, 2,4-dimethyl-5-phenyl-pentanitrile via oxidation dehydration chemistry by reaction of hydroxylamine/formic acid as described above.

The substituted 5-phenylpentanols may readily be converted to the reverse ester form, i.e. where Z in the above formula is —CH$_2$OC(O)CH$_3$ by reaction with acetic anhydride or acetic acid. Such reactions may be conducted with or without the aid of a catalyst, and an inert solvent, such as toluene, may be used with the application of heat to drive the reaction if necessary. in a like manner, the substituted 5-phenylpentanoic acids may be converted to the corresponding ester by reaction with an appropriate alcohol. Such esterification reactions are well known and widely referred to in the chemical literature, for example in "Advanced Organic Chemistry", Jerry March, 4th Edition (1992), Sections 0–21 and 0–22, pp 392–393.

The substituted 5-phenylpentane derivatives of the present invention possess varied fragrance notes. In general, those compounds where Z in the general formula given above is —CN have a green, pleasant, linen, slightly rosy fragrance. Those compounds of the above general formula where Z is —CHO possess a citrus ozone fragrance. Those compounds where Z in the general formula is —CH$_2$OH have odors which are less intense but more tenacious and rosy than the corresponding aldehydes, and the esters where Z is —COOCH$_3$ or —CH$_2$OC(O)CH$_3$ have fruity-floral notes. The unique fragrance notes of the subject compounds make them useful in imparting, augmenting or enhancing the olfactory component in perfume or perfume articles whether that component is intended to impart a characteristic perfume to the article or mask or modify the odor of one or more of the components thereof. The specific examples, which follow, demonstrate the versatility of these materials.

As those skilled in the art will appreciate, fragrant materials are typically utilized in combinations that may include both natural and synthetic ingredients to achieve the desired overall perfume effect. The substituted 5-phenylpentane derivatives as contemplated herein possess unique fragrant notes and, therefore, are particularly useful individually and in such combinations in perfumes and perfumed articles, such as cosmetics, soaps, air fresheners, various detergent formulations, especially those containing lipase, and other household products. The substituted 5-phenylpentane derivatives within the present invention may be utilized individually or combined in any proportion and are particularly advantageous in products such as laundry detergent powders and liquids with or without added bleach activators, liquid and powdered cleaners containing chlorine as the active bleaching agent, acid and alkaline household cleaners, toilet soaps, fabric softeners, haircare products, such as shampoos, and air fresheners.

As is conventional in the art, the desired amount of a fragrant material to be added to a given preparation or product is determined by the nature of the product and other factors, such as whether the object is to create a particular fragrance as in a perfume or effectively mask the natural odor of other ingredients in the product to enhance acceptance by the user. The fragrant material is combined with the product in intimate admixture. Typically, where a fragrance component is a combination of a number of fragrance materials, they are combined and formulated to achieve the desired fragrant effect and then admixed with the product.

The choice of a carrier, e.g. a solvent or solvent mixture, if any, to be utilized in achieving the desired intimate admixture with the final product is considered to be within the skill of the art. The amount of individual substituted 5-phenylpentane derivatives or mixtures thereof in a perfume or perfumed article in accordance with the present invention is generally not greater than about 1% by weight based on the weight of the final product and can vary from about 0.01% to about 1% preferably from about 0.05% to about 0.2% by weight. The substituted 5-phenylpentane derivatives of the present invention are particularly advantageous for use as fragrant materials in such preparations because they are cost effective to produce and are projected to be biodegradable.

The following examples further illustrate the invention, but are in no way intended to be limiting thereon.

EXAMPLE 1

Preparation of 4-methyl-5-phenylpentanitrile

A mixture of 2-methyl-3-phenylpropanal (113 g., 0.76 mol.), cyanoacetic acid (66 g., 0.77 mol.) ammonium acetate (5.86 g. 0.08 mol), pyridine (75 ml), and toluene (160 ml) was refluxed for two hours with azeotropic removal of water. The reaction a mixture was diluted with 400 ml of toluene, washed with two 200 ml portions of water, three 200 ml portions of 2 N hydrochloric acid, 200 ml of a saturated aqueous solution of sodium bicarbonate, and 200 ml of saturated sodium chloride, dried over magnesium sulfate and concentrated. The residue was distilled to afford 106 g. of 4-methyl-5-phenylpent-2-enitrile (82% yield) as four isomers; bp 106–109° C. at 0.4 mm. Odor: pleasant citrus.

A suspension of 4-methyl-5-phenylpent-2-enitrile (50 g., 0.3 mol) 200 ml of ethanol and 5% palladium of carbon (2.66 g.) was shaken under 60 psi of hydrogen in a Parr apparatus at room temperature for four hours. The reaction mixture was diluted with 200 ml tert-butyl methylether, filtered, washed with two 100 ml portions of water, dried over magnesium sulfate, and concentrated. The residue was distilled to afford 41 g. of 4-methyl-5-phenylpentanitrile 80% yield; bp 84–90° C. at 0.6 mm. Odor: pleasant green, linen, slightly rosy. $^1$H NMR (CDCl$_3$) 7.31-7.13 (m, 5H), 2.63-2.57 (m 1H),2.50–2.25 (m 3H), 1.95–1.85 (m, 1H), 1.79–1.69 (m, 1H), 1.52–1.42 (m, 1H), 1.43 (d,J=6.6 Hz, 3H).

The reaction was repeated utilizing an equimolar quantity of dimethyl malonate in place of the cyanoacetic acid to yield methyl 4-methyl-5-phenylpentanoate. Repeating the cyanoacetic acid condensation/reduction reaction utilizing 5phenylpentan-3-one as the starting material afforded 3-ethyl-5-phenylpentanenitrile.

EXAMPLE 2

Preparation of 4-methyl-5-phenylpentanal

To a cooled of 4-methyl-5-phenylpentanitrile (38.2 g, 0.22 mol.) in 200 ml of toluene at -60° C. (dry ice/isopropanol) was added a solution of diisobutylaluminum hydride in toluene (1.5 M, 160 ml, 0.24 mol) over a period of one hour. The reaction mixture was then allowed to warm to room temperature and stirred for fifteen minutes.

Quenching was accomplished by cooling the mixture to 5° C., and thereafter adding 50 ml saturated aqueous ammonium chloride followed by 350 ml of 4 M hydrochloric acid. The resulting mixture was filtered, the organic phase washed with 200 ml of saturated aqueous sodium bicarbonate and saturated aqueous sodium chloride, dried over magnesium sulfate and concentrated. The residue was distilled to afford 41 g. of 4-methyl-5-phenylpentanal (90% yield) Odor-citrus ozone; bp 83–90° C. at 0.5 mm. Mass Spectrum from 5358–59. MS (EI) m/z (relative intensity) 176 (M+, 20), 158 (M+–$H_2O$, 2).

EXAMPLE 3

Preparation of 2,4-dimethyl-5-phenyl-pentanal

Into a 2 L Morton flask equipped with a mechanical air stirrer, temperature probe, Nitrogen inlet, autojack, and cooling bath was placed methanol (350 mL) and NaOH (31.25 g, 0.78 mol) dissolved in water (93.75 mL). 2-Methyl-3-phenyl-propanal (100 g, 0.68 mol) was added to the resulting mixture with stirring at 20° C. Over a period of 5 hours at an exponentially decreasing rate, propionaldehyde (48.82 mL, 39.25 g, 0.68 mol) was added to the mixture via a syringe pump while maintaining the reaction temperature at 14–20° C. The following propionaldehyde addition rate profile was used: 0.179 mL/min for two hours; 0.162 mL/min for one hour; and 0.147 mL/min for two hours. The reaction mixture was stirred for an additional 20 min at 14–20 ° C. Acetic acid (47 mL) was then added to the reaction mass followed by 100 mL of a saturated aqueous solution of sodium chloride. The mixture was extracted with two 100 mL portions of MTBE. The organic layers were combined and washed with two 100 mL portions of a saturated aqueous solution of sodium bicarbonate solution then with a saturated aqueous solution of.sodium chloride, dried ($MgSO_4$), filtered, and roto-evaporated to give 2,4-dimethyl-5-phenylpent-2-enal as a yellow liquid isomeric mixture (118.9 g).

A portion of the crude Aldol condensation product formed above (60 g, 0.32 mol was dissolved in 100 ml of ethanol and hydrogenated over 5% Pd/C (0.6 g) at 50 psi, 25° C. The mixture was filtered through celite, roto-evaporated then purified by vacuum distillation by a Kugelrohr apparatus to afford 2,4-dimethyl-5-phenylpentanal, odor-green, grassy, floral-hyacinth.

In a similar manner, utilizing 3-phenyl propanal as the starting material, there was prepared 2-methyl-5-phenylpentanal, odor- soft, green, fatty ozone.

EXAMPLE 4

Preparation of 2,4-dimethyl-5-phenylpentan-1-ol

Into a one liter flask equipped with a mechanical air stirrer, temperature probe, nitrogen inlet, autojack, and cooling bath was placed 50 mL methanol, 2,4-dimethyl-5-phenylpentanal (50.0 g, 0.26 mol), and acetic acid (11.0 g, 0.18 mol). To the stirred solution was added $NaBH_4$ (70 g, 0.18 mol) in 50 mL of methanol over a period of two hours while maintaining the reaction temperature at 20° C. Water was then added until the all materials went into solution and 200 mL methyl t-butyl ether was then added. The organic phase was isolated, washed with three 50 mL portions of saturated NaCl solution, dried over magnesium sulfate, filtered, and rotovapped to give the product as a colorless liquid (49.9 g), odor—fresh, green herbal.

EXAMPLE 5

Preparation of 2-methyl-5-phenylpentanenitndle

The saturated aldehyde, 2-methyl-5-phenylpentanal (36.8 g, 0.194 mol), hydroxylamine hydrochloride (22.5 g, 0.324 mol) and formic acid (245 g) were combined and heated at reflux for 0.5 h. The reaction solution was cooled and diluted with 500 mL of water. The organic layer was removed and the aqueous phase extracted with four 100 mL portions of methyl t-butyl ether. The organic layers were combined and washed with two 250 mL portions of 5% NaOH solution, followed by three 200 mL portions of saturated $NaHCO_3$ solution dried over magnesium sulfate and rotovapped to obtain 36.2 g of crude product. The product was purified by vacuum distillation via Kugelrohr apparatus, odor - herbaceous, citrus, spicy.

We claim:

1. A fragrance material, wherein said material is 2,4-dimethyl-5-phenylpentanal.

2. A perfume or perfumed article containing as at least a portion of its fragrant component a fragrance-imparting amount of 2,4-dimethyl-5-phenylpentanal.

3. A method of imparting, enhancing or augmenting the fragrance of a perfume or perfumed article comprising adding thereto a fragrance-imparting amount of 2,4-dimethyl-5-phenylpentanal.

* * * * *